United States Patent
Wang et al.

(10) Patent No.: US 10,737,111 B2
(45) Date of Patent: Aug. 11, 2020

(54) X-OPTOGENETICS / U-OPTOGENETICS

(71) Applicant: Rensselaer Polytechnic Institute, Troy, NY (US)

(72) Inventors: Ge Wang, Loudonville, NY (US); Matthew Getzin, Troy, NY (US); Rachel Berry, Basking Ridge, NJ (US); Lars Gjesteby, Cohasset, MA (US)

(73) Assignee: Rensselaer Polytechnic Institute, Troy, NY (US)

( * ) Notice: Subject to any disclaimer, the term of this patent is extended or adjusted under 35 U.S.C. 154(b) by 246 days.

(21) Appl. No.: 14/971,777

(22) Filed: Dec. 16, 2015

(65) Prior Publication Data

US 2016/0166852 A1    Jun. 16, 2016

Related U.S. Application Data

(60) Provisional application No. 62/092,687, filed on Dec. 16, 2014.

(51) Int. Cl.
*A61N 5/06* (2006.01)
*A61K 41/00* (2020.01)

(52) U.S. Cl.
CPC .......... *A61N 5/0622* (2013.01); *A61K 41/008* (2013.01); *A61N 2005/0656* (2013.01)

(58) Field of Classification Search
CPC .......... A61N 5/0622; A61N 2005/0656; A61N 2005/1022; A61N 5/10
USPC ....................................................... 128/898
See application file for complete search history.

(56) References Cited

U.S. PATENT DOCUMENTS

| 7,227,924 B2* | 6/2007 | Zhou ................. A61B 6/032 378/10 |
| 7,505,562 B2* | 3/2009 | Dinca ................. G01N 23/201 378/57 |
| 8,447,013 B2* | 5/2013 | Sprenger ............ H01J 35/04 378/122 |
| 8,971,484 B2* | 3/2015 | Beckmann ........... G01V 5/005 378/122 |
| 2011/0286581 A1* | 11/2011 | Sprenger ............ H01J 35/04 378/113 |
| 2014/0219922 A1 | 8/2014 | Shuba |
| 2014/0323946 A1* | 10/2014 | Bourke, Jr. ........ A61K 41/0085 604/20 |

OTHER PUBLICATIONS

Reyes-Mena et al. "Miniature X-Ray Tubes Utilizing Carbon-Nanotubebased Cold Cathodes". JCPDS—International Centre for Diffraction Data 2005, Advances in X-ray Analysis, vol. 48.*

(Continued)

*Primary Examiner* — Suba Ganesan
*Assistant Examiner* — Aren Patel
(74) *Attorney, Agent, or Firm* — Murtha Cullina LLP; Anthony P. Gangemi

(57) ABSTRACT

Methods and systems for performing optogenetics using X-rays or ultrasound waves are provided. Visible-light-emitting nanophosphors can be provided to a sample, and X-ray stimulation can be used to stimulate the nanophosphors to emit visible light. Alternatively, ultrasonic waves can be provided to the sample to cause sonoluminescence, also resulting in emission of visible light, and this can be aided by the use of a chemiluminescent agent present in the sample. The emitted light can trigger changes in proteins that modulate membrane potentials in neuronal cells.

7 Claims, 2 Drawing Sheets

(56) References Cited

OTHER PUBLICATIONS

Adams, Amy., "Optogenetics Earns Deisseroth Keio Prize in Medicine," Stanford Medicine, published Sep. 10, 2014, p. 1-7, <https://med.stanford.edu/news/all-news/2014/09/optogenetics-earns-deisseroth-keio-prize-in-medicine.html>.

Ahmad, Moiz et al. "X-Ray Luminescence and X-Ray Fluorescence Computed Tomography: New Molecular Imaging Modalities," *IEEE Access*, 2, pp. 1051-1061, (2014).

Ajithkumar, G. et al. "Multimodal Bioimaging Using a Rare Earth Doped $Gd_2 O_2S$: Yb/Er Phosphor With Upconversion Luminescence and Magnetic Resonance Properties," *Journal of Materials Chemistry B*, 1(11), pp. 1561-1572, Royal Society of Chemistry (2013).

Arenkiel, Benjamin R. et al. "In Vivo Light-Induced Activation of Neural Circuitry in Transgenic Mice Expressing Channelrhodopsin-2," *Neuron*, 54(2), pp. 205-218, Elsevier (2007).

Berndt, Andre et al. "Structure-Guided Transformation of Channelrhodopsin into a Light-Activated Chloride Channel," Science, 344(6182), American Association for the Advancement of Science, (2014), Abstract only.

Cao, Tianye et al. "Water-Soluble $NaYF4$:Yb/Er Upconversion Nanophosphors: Synthesis, Characteristics and Application in Bioimaging," *Inorganic Chemistry Communications*, 13(3), pp. 392-394, (2010).

Chatterjee, Krishnendu et al. "Core/Shell Nanoparticles in Biomedical Applications," *Adv. Colloid Interface Sci.*, 209, pp. 8-39, Elsevier, (2014).

Chen, Hongyu et al., "Monitoring pH-Triggered Drug Release from Radioluminescent Nanocapsules with X-ray Excited Optical Luminescence," *ACS Nano* 7(2), pp. 1178-1187, ACS Publications, (2013).

Chen, J.-Y., et al. "Efficiency Improvement of Si Solar Cells Using Metal-Enhanced Nanophosphor Fluorescence," *Solar Energy Materials & Solar Cells*, 120, pp. 168-174, (2014).

Chuang, Yen-Jun et al.,"Photostimulable Near-Infrared Persistent Luminescent Nanoprobes for Ultrasensitive and Longitudinal Deep-Tissue Bio-Imaging," *Theranostics*, 4(11), pp. 1112-1122, Ivyspring International Publisher (2014).

Clements, Isaac P. et al. "Miniaturized LED Sources for In Vivo Optogenetic Experimentation," *Proc. SPIE* vol. 8586, (2013), Abstract only.

Cong, Wenxiang et al. "X-Ray Fluorescence Computed Tomography With Polycapillary Focusing," *Access, IEEE*, (2014).

Dąbrowski, K. M. et al. "X-ray Imaging Inside the Focal Spot of Polycapillary Optics Using the Coded Aperture Concept," *Optics Express*, 21(3), pp. 2920-2927, Optical Society of America (2013).

De La Fuente, Jesus M. et al. "Nanoparticle targeting at cells," *Langmuir*, 22(7), pp. 3286-3293, ACS Publications (2006).

Dhanaraj, J., et al. "Photoluminescence Characteristics of $Y2O3$: $Eu^{3+}$ Nanophosphors Prepared Using Sol-Gel Thermolysis," *J. Phys. Chem. B*, 105(45), pp. 11098-11105, ACS Publications, (2001).

Dhoble, S. J. et al. "$Ce^{3+}$ and $Eu^{3+}$ activated $Na_2Sr_2Al_2PO_4F_9$ nanophosphor," *Advanced Materials Letters*,2(5), pp. 349-353, (2011).

Di Fabrizio, E. et al. "High-efficiency Multilevel Zone Plates for keV X-rays," *Nature*, 401(6756), pp. 895-898, Nature Publishing Group, (1999).

Dong, Kai et al. "Ultrasmall biomolecule-anchored hybrid $GdVO_4$ nanophosphors as a metabolizable multimodal bioimaging contrast agent," *Nanoscale*, 6(20), pp. 12042-12049, Royal Society of Chemistry, (2014).

Entcheva, Emilia, et al. "Channelrhodopsin2 Current During the Action Potential: "Optical AP Clamp" and Approximation," *Scientific Reports* 4, pp. 1-7, Nature Publishing Group, (2014).

Erickson, Harold P., "Size and Shape of Protein Molecules at the Nanometer Level Determined by Sedimentation, Gel Filtration, and Electron Microscopy," Biological Procedures Online, 11(1), pp. 32-51, Springer (2009).

Farah, Nairouz et al., "Patterned Optical Activation of Retinal Ganglion Cells," *Conference Proc IEEE Eng Med Biol Soc*, pp. 6368-6370, (2007).

Fenno, Lief et al. "The Development and Application of Optogenetics," *Annual Review Neurosci.* 34, 389-412, pp. 389-412, Annual Reviews, 2011.

Fessenden, Jim, "EUREKA Grant to Fund Development of New 'Optogenetic' Technique for Mapping Neural Networks at UMMS," AAAS, pp. 1-4, (2013).

Gao, Kepan et al. "Influence of Particle Size on Transport of Methotrexate Across Blood Brain Barrier by Polysorbate 80-coated Polybutylcyanoacrylate Nanoparticles.," *International Journal of Pharmaceutics*, 310(1-2), pp. 213-219, (2006).

Gorokhova, E. I. et al. "Luminescence and Scintillation Properties of Gd2O2S: Tb Ce Ceramics," *IEEE Trans. Nucl. Sci.* 52(6), pp. 3129-3132, Institute of Electrical and Electronics Engineers, (2005).

Grossman, Nir, et al., "Multi-site Optical Excitation Using ChR2 and Micro-LED array," *J Neural Eng*, 7(1), pp. 1-13, (2010).

Gupta, Ajay Kumar et al. "Synthesis and Surface Engineering of Iron Oxide Nanoparticles for Biomedical Applications," *Biomaterials*, 26(18), pp. 3995-4021, Elsevier (2005).

He, Yonghong et al. "In Vivo Sonoluminescence Imaging With the Assistance of FCLA," *Phys. Med. Biol.* 47(9), pp. 1535-1541, IOP Publishing, 2002.

Hegemann, Peter et al. "Channelrhodopsin Engineering and Exploration of New Optogenetic Tools," *Nature Methods*, 8(1), pp. 39-42, Nature Publishing Group (2011).

Hilgenfeldt, Sascha et al. "A Simple Explanation of Light Emission in Sonoluminescence," *Nature* 398 (6726), pp. 402-405, Nature Publishing Group (1999).

Jadhav, A. P. et al. "Red Emitting $Y2O3$:$Eu^{3+}$ Nanophosphors With >80% Down Conversion Efficiency†," *J. Mater. Chem. C*, 2, pp. 496-500 (2014).

Jagdeo, Jared R. et al. "Transcranial Red and Near Infrared Light Transmission in a Cadaveric Model," *PLoS One*, 7(10), e47460, pp. 1-10, Public Library of Science, (2012).

Jia, Zhiheng et al., "Stimulating Cardiac Muscle by Light: Cardiac Optogenetics by Cell Delivery," *Circ. Arrhythmia Electrophysiol.*, 4(5), pp. 753-760, Am Heart Assoc, (2011).

Kim, Minsung et al. "A Highly Luminous $LiCaPO_4$:$Eu^{2+}$ Phosphor Synthesized by a Solution Method Employing a Water-Soluble Phosphate Ester," *Opt. Photonics J.*, 3, pp. 13-18, Scientific Research Publishing , (2013).

Li, Le-Le et al. "Biomimetic Surface Engineering of Lanthanide-Doped Upconversion Nanoparticles as Versatile Bioprobes," *Angewandte Chemie*, 124(25), pp. 6225-6229, Wiley Online Library, (2012).

Liu, Feng et al. "Photostimulated Near-Infrared Persistent Luminescence as a New Optical Read-Out From $Cr^{3+}$-doped $LiGa_5O_8$," *Scientic Reports*, 3, pp. 1-9, Nature Publishing Group, (2013).

Lutz, Christoph, et al., "Holographic Photolysis of Caged Neurotransmitters," *Nature Methods*, 5(9), pp. 821-827, (2008).

Mattis, Joanna et al. "Principles for Applying Aptogenetic Tools Derived From Direct Comparative Analysis of Microbial Opsins," *Nature Methods*, 9(2), pp. 159-172, (2012).

Moore, Thomas L. et al. "Polymer-Coated Radioluminescent Nanoparticles for Quantitative Imaging of Drug Delivery," *Advanced Functional Materials*, 24(37), pp. 5815-5823, Wiley Online Library, (2014).

Nagel, Georg et al. "Channelrhodopsin-2, a Directly Light-gated Cation-selective Membrane Channel," *Proc. Natl. Acad. Sci.*, 100(24), pp. 13940-13945, National Acad Sciences, (2003).

Olesiak-Banska, J., et al. "Synthesis and Optical Properties of Water-Soluble Fluoride Nanophosphors Co-doped with $Eu^{3+}$ and $Tb^{3+}$," *Optical Materials*, 33(9), pp. 1419-1423, (2011).

"Radiation Dose in X-Ray and CT Exams.", *Radiol. Soc. North Am. Inc.*, 2014, [online webpage retrieved Mar. 11, 2016] from: http://www.radiologyinfo.org/en/safety/?pg=sfty_xray, pp. 1-6.

Raimondo, Joseph V. et al. "Optogenetic Silencing Strategies Differ in Their Effects on Inhibitory Synaptic Transmission," *Nature Neuroscience*, 15(8), pp. 1102-1104, Nature Publishing Group (2012).

(56) References Cited

OTHER PUBLICATIONS

Romanov, A. Yu, "Optic Parameters of a Middle-Focus Kumakhov Lens for Hard X-rays," *Technical Physical Letters*, 31(3), pp. 200-201, Springer (2005).
Shaik, Niyaz Parvin "Photoluminescence Studies on $Sr_2CeO_4$ Nanophosphor," *World Journal of Chemistry*, 6(2), pp. 115-117, (2011).
Shen, Chen et al. "Anisotropic Complementary Acoustic Metamaterial for Canceling out Aberrating Layers," *Physical Review X* 4(4), pp. 041033-1-041033-7, American Physical Society (2014).
Sowell, Elizabeth R. et al. "Longitudinal Mapping of Cortical Thickness and Brain Growth in Normal Children," *Journal Neuroscience*, 24(38), pp. 8223-8231, Soc Neuroscience, (2004).
Stark, Glenn, "X-ray," Encyclopedia Brittanica, published Aug. 20, 2014, pp. 1-5, <http://www.britannica.com/science/X-rays>.
Stolik, S., et al. "Measurement of the Penetration Depths of Red and Near Infrared Light in Human 'Ex Vivo' Tissues," *Journal Photochemistry B Biology*, 57(2), pp. 90-93, Elsevier, (2000).
Sun, Conroy et al. "Facile Synthesis of Amine-Functionalized $Eu^{3+}$-Doped $La(OH)_3$ Nanophosphors for Bioimaging," *Nanoscale Res. Lett*, 6(24), pp. 1-7, (2011).
Sun, Conroy et al. Synthesis and Radioluminescence of PEGylated Eu3+-doped Nanophosphors as Bioimaging Probes. *Advanced Materials*, 23(24), pp. H195-H199, (2011).
Sun, Yun et al. "Upconversion Nanophosphors $NaluF_4$: Yb, Tm for Lymphatic Imaging In Vivo by Real-Time Upconversion Luminescence Imaging Under Ambient Light and High-Resolution X-ray CT," *Theranostics*, 3(5), 346-353, Ivyspring International Publisher, (2013).
Uegaki, Koichi et al. "Archaerhodopsin-2, from *Halobacterium* sp. aus-2 Further Reveals Essential Amino Acid Residues for Light-Driven Proton Pumps," *Archives of Biochemistry and Biophysics*, 286(1), pp. 107-110, Elsevier (1991).
Van Hao, Bui et al. "Synthesis of $Y_2O_3$: $Eu^{3+}$ Micro-and Nanophosphors by Sol-Gel Process," *J. Phys. Conf. Ser.*, 187(1), pp. 1-6, 12074, IOP Publishing (2009).
Yadav, Raghvendra Singh et al. "Blue-Shift and Enhanced Photoluminescence in $BaMgAl_{10}O_{17}$: $Eu^{2+}$ Nanophosphor under VUV Excitation for PDPs Application," *Materials Science and Applications*, 1(01), pp. 25-31, Scientific Research Publishing, (2010).
Yizhar, Ofer et al. "Optogenetics in Neural Systems," *Neuron*, 71(1), pp. 9-34, Cell Press (2011).
Yue, G. Z. et al. "Generation of Continuous and Pulsed Diagnostic Imaging x-ray Radiation Using a Carbon-Nanotube-Based Field-Emission Cathode," *Appl. Phys. Lett.*, 81(2), pp. 355-357, (2002).
Zako, Tamotsu et al. "Improvement of Dispersion Stability and Characterization of Upconversion Nanophosphors Covalently Modified With PEG as a Fluorescence Bioimaging Probe," *J. Mater. Sci.*, 43(15), pp. 5325-5330, Springer, (2008).
Zhang, J., et al. "Stationary Scanning X-Ray Source Based on Carbon Nanotube Field Emitters," *Applied Physics Letters*, 86(18), pp. 184104-1-184104-3, AIP Publishing (2005).
Zhou, Jing et al. "Enhancement of Fluoresceinyl Cypridina Luciferin Analog Chemiluminescence by Human Serum Albumin for Singlet Oxygen Detection," *Photochemistry and Photobioloy*, 82(4), pp. 1058-1064, (2006).
Zhou, Yu at "Impact of Single-chain Fv Antibody Fragment Affinity on Nanoparticle Targeting of Epidermal Growth Factor Receptor-expressing Tumor Cells," *J. Mol. Biol.*, 371(4), pp. 934-947, Elsevier (2007).
Agrisera Antibodies Product Information, [online webpage retrieved Mar. 25, 2016]from:<http://www.agrisera.com/cgibin/ibutik/SkapaFaktura.pl?SkrivPDF=J&funk=visa_artikel&artnr=AS12___1851&Friendly_Grupp=bacterialinsect-and-fungal-&Friendly=nphr-halorhodopsin-&artgrp=28&Sprak=en>, pp. 1-3.
Barber, Ted et al. "The Density of Tissues In and About the Head," *Acta Neurol. Scand.* 46(1), pp. 85-92, Wiley Online Library, (1970).
Berndt, Andre et al. "Structure-Guided Transformation of Channelrhodopsin into a Light-Activated Chloride Channel," *Science*, 344(6182), American Association for the Advancement of Science, pp. 420-424, (2014).
Chen, Hongyu et al. Monitoring pH-triggered Drug Release From Radioluminescent Nanocapsules With X-ray Excited Optical Luminescence. *ACS Nano*, 7(2), pp. 1178-1187, (2013).
Chen, Hongyu et al. "Multifunctional Yolk-in-Shell Nanoparticles for pH-triggered Drug Release and Imaging," *Small*, 10(16), pp. 3364-3370, (2014).
Clements, Isaac P. et al. "Miniaturized LED Sources for In Vivo Optogenetic Experimentation," *Proc. SPIE*, vol. 8586, pp. 1-9, (2013).
Deisseroth, Karl, "Optogenetics: Controlling the Brain with Light [Extended Version]," *Scientific American*, [online article retrieved Mar. 31, 2016] from http://www.scientificamerican.com/article/optogenetics-controlling/, (2010), pp. 1-19.
"Energy and Work Unit Conversion," *Advamed, Inc.*,[online webpage retrieved Mar. 25, 2016] from <http://www.unitconversion.info/energy.html>, pp. 1-4.
Knopfel, T., et al. "Optogenetics: Tools for Controlling and Monitoring Neuronal Activity," pp. 8, *Elsevier*, (2012).
Frenzel, H. et al. "Luminescence in Water Carrying Supersonic Waves," Z. Phys., 27, pp. 421-424, (1934).

\* cited by examiner

X-OPTOGENETICS / U-OPTOGENETICS

CROSS-REFERENCE TO A RELATED APPLICATION

The present application claims the benefit of U.S. Provisional Application Ser. No. 62/092,687, filed Dec. 16, 2014, which is incorporated by reference herein in its entirety, including any figures, tables, and drawings.

BACKGROUND OF INVENTION

Optogenetics is an established technique that uses visible light to modulate membrane voltage in neural cells. The visible light can be used to trigger changes in proteins that modulate membrane potentials in neuronal cells through excitatory or inhibitory membrane currents. This ability to modulate neuronal cells has proven instrumental in preclinical studies and holds enormous potential for the treatment of diseases such as Parkinson's, epilepsy, and depression. However, current techniques used for optogenetic control are too invasive for clinical applications. That is, although optogenetics allows researchers to study parts of the brain like never before, it is limited because it is invasive, and visible light cannot travel very deeply into tissue.

BRIEF SUMMARY

Optogenetics is a useful technique that allows for deep insight in the field of neuroscience and neuropathology and has been adopted to study the roles of various neurons in disease states such as Parkinson's, epilepsy, and depression. However, these applications have been limited in their scopes because of the invasive nature and depth limitation of related art optogenetics systems and methods. There is a critical and immediate need to improve optogenetics for deeper and non-invasive applications.

The subject invention addresses this need by providing novel and advantageous methods and systems for performing optogenetics using X-rays and/or ultrasound waves. Light-emitting particles can be provided to a target area (e.g., a brain of an animal such as a human or other mammal) and then stimulated by X-rays or ultrasound waves. The stimulation can cause the particles to emit light (e.g., visible light). The emitted light can trigger changes in proteins that modulate membrane potentials in neuronal cells. The light-emitting particles can be, for example, light-emitting nanophosphors (NPs) (e.g., visible-light-emitting nanophospors) or chemiluminescent agents (e.g., fluoresceinyl Cypridina luminescent analog).

In an embodiment, a method of performing optogenetics can include: providing light-emitting particles to a sample; and providing X-rays to the sample such that the X-rays cause the light-emitting particles to emit light, thereby changing the membrane potential of a neuron within the sample. The light-emitting particles can be visible-light-emitting nanophosphors, such that the nanophosphors emit light in the visible spectrum upon stimulation by the X-rays, and the X-rays can be provided by a carbon nanotube X-ray source.

In another embodiment, a method of performing optogenetics can include: providing chemiluminescent agents to a sample; and providing ultrasonic waves to the sample causing a sonoluminescence effect within the sample and also causing the chemiluminescent agents to emit light, thereby changing the membrane potential of a neuron within the sample. The chemiluminescent agents can be fluoresceinyl Cypridina luminescent analog (FCLA) molecules.

DETAILED DISCLOSURE

Figure 1:
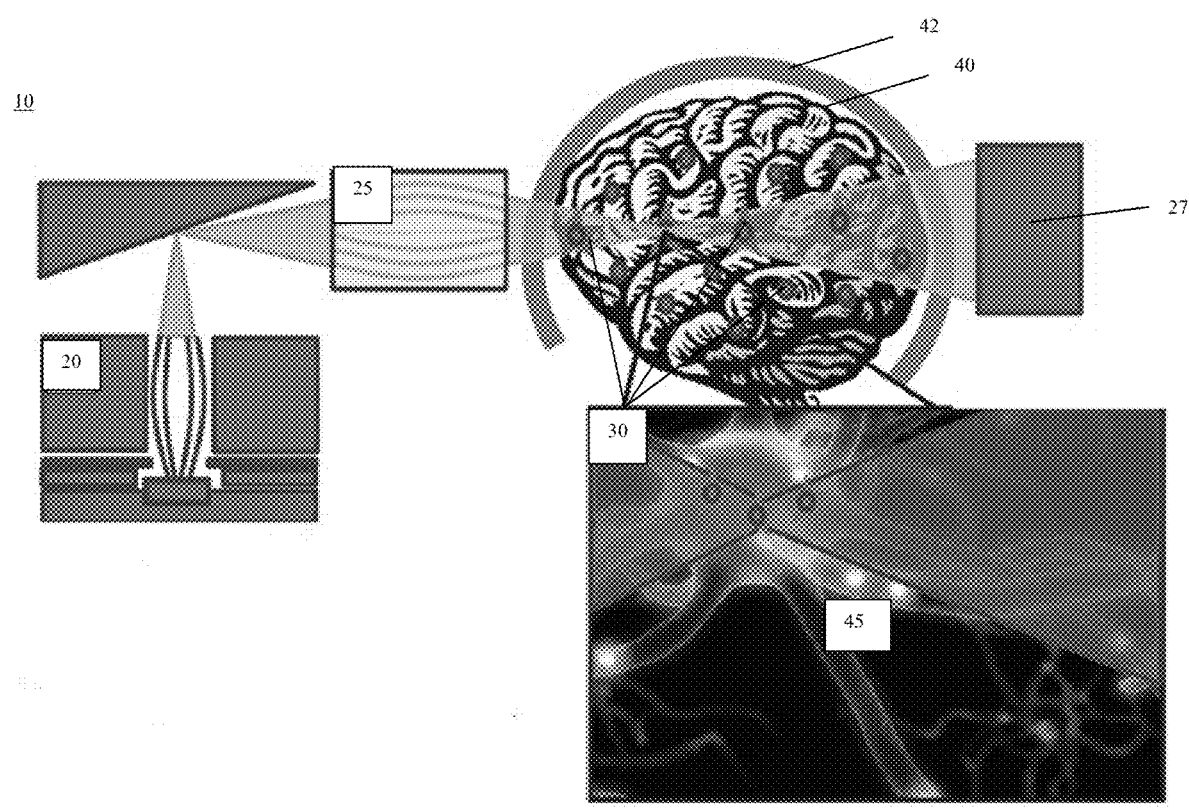
FIG. 1 shows a schematic view of an X-ray optogenetic system according to an embodiment of the subject invention.

The subject invention provides novel and advantageous methods and systems for performing optogenetics using X-rays and/or ultrasound waves. Light-emitting particles can be provided to a target area (e.g., a brain of an animal such as a human or other mammal) and then stimulated by X-rays or ultrasound waves. The stimulation can cause the particles to emit light (e.g., visible light). The emitted light can trigger changes in proteins that modulate membrane potentials in neuronal cells. The light-emitting particles can be, for example, light-emitting nanophosphors (NPs) (e.g., visible-light-emitting nanophospors) or chemiluminescent agents (e.g., fluoresceinyl Cypridina luminescent analog).

Optogenetics can use rhodopsins, such as channelrhodopsin2 (ChR2), to induce excitatory potentials in transfected neurons of animals. ChR2 is a transmembrane ion channel found in green algae that becomes permeable to cations in the presence of blue light. ChR2 can be used in neurons because ion channels are a main contributor in electrical signal transduction in the brain. Optogenetics allows researchers to target specific areas of the brain and study how modulated neuron firing affects downstream behaviors and cellular processes. Also, other light-sensitive transmembrane proteins that regulate the transmembrane voltage by maintaining ion concentrations on either side of the membrane can be used in the field of optogenetics. Halorhodpsin (NphR) and archeorhodopsin (Arch) are two such proteins and can be referred to as ion pumps. Both channels and pumps can be further generalized into the protein group called rhodopsins.

A typical optogenetics technique can include transfecting specified neuronal cells with DNA encoding for the appropriate rhodopsin for the application. Upon expression of these proteins, a light fiber can be surgically implanted into the organism's brain so light at the stimulating wavelengths can directly irradiate neurons and modulate their membrane current. Such current modulation comes in two forms that depend on the ions to which the channel becomes permeable in its open state. The cation-specific channels lead to membrane depolarization (excitatory), and the proton/anion-specific pumps cause the membrane to hyperpolarize (inhibitory). In this way, the membrane current can be directly controlled by a light source, which in related art applications is in the form of either a laser or a light-emitting diode (LED). Both sources have limitations. Lasers are very costly, while the light from an LED is spread out and not a focused beam, so it cannot be accurately targeted as a laser can.

Current practice of optogenetics is performed on a macroscopic scale. For example, ChR2-expressing cells have been activated by a 470-490 nm light in a power range of 1-20 mW/mm$^2$ with pulse duration of 5-100 ms. This type of stimulation results in a ChR2-channel driven membrane current that peaks around −9 pA/pF. In these instances, the studied tissue is flooded with light and any cell within a few millimeters of the source that is expressing rhodopsins will have modulated membrane currents that may lead to distinct network and/or behavioral changes. X-ray optogenetic and ultrasound optogenetic techniques of the subject invention can shift the scale from the macroscopic to a microscopic or even nanoscopic level of control.

Because of the invasive nature or limited penetration of LEDs and laser sources, infrared radiation has been used with upconversion nanoparticles (UCNPs). After excitation, these nanoparticles emit photons of visible light whose wavelengths can be customized based on the particle chemistry. These emissions can then be used to modulate the membrane current. This method is less invasive than those that use LEDs or lasers. Despite this incremental improvement to the optogenetic approach, infrared (IR) light has its limitations as well. IR penetration through the skull is about 4-10% of the initial intensity, and IR light at 868 nm only penetrates brain tissue enough to gain access to a fraction of human cortical neurons, as the human cortex thickness is typically in the range of 2-5.5 mm.

FIG. 1 shows a schematic view of an X-ray optogenetic system 10 according to an embodiment of the subject invention. Referring to FIG. 1, an X-ray source 20 can provide X-rays, which can be focused through an optional focusing element 25. Light-emitting particles 30 can be provided to a focus area (e.g., a mammal brain 40), and can emit light (e.g., visible light) upon stimulation by the X-rays. Light-sensitive ion channels 45 within the focus area can receive light as a stimulus and open to allow for ion flow, thereby changing the membrane potential and possibly stimulating an action potential. The light-emitting particles 30 can be nanophosphors (NPs), such as visible-light-emitting NPs, though embodiments are not limited thereto. The optional focusing element 25 can be, for example, a lens such as a poly-capillary lens. In an embodiment, the X-ray source 20 can include a carbon nanotube cathode emitting electrons that are focused onto an anode through a gate and/or focusing electrode. An optional X-ray stop (or detector) 27 can also be present to collect any unabsorbed X-ray radiation.

The light-sensitive ion channels 45 can open, for example, at least 30% of the time after receiving a single photon as a stimulus. In one embodiment, the light-sensitive ion channels 45 can open about 30%-70% of the time after receiving a single photon as a stimulus. In an alternative embodiment, the light-sensitive ion channels 45 can open at least 70% of the time after receiving a single photon as a stimulus.

Figure 2:
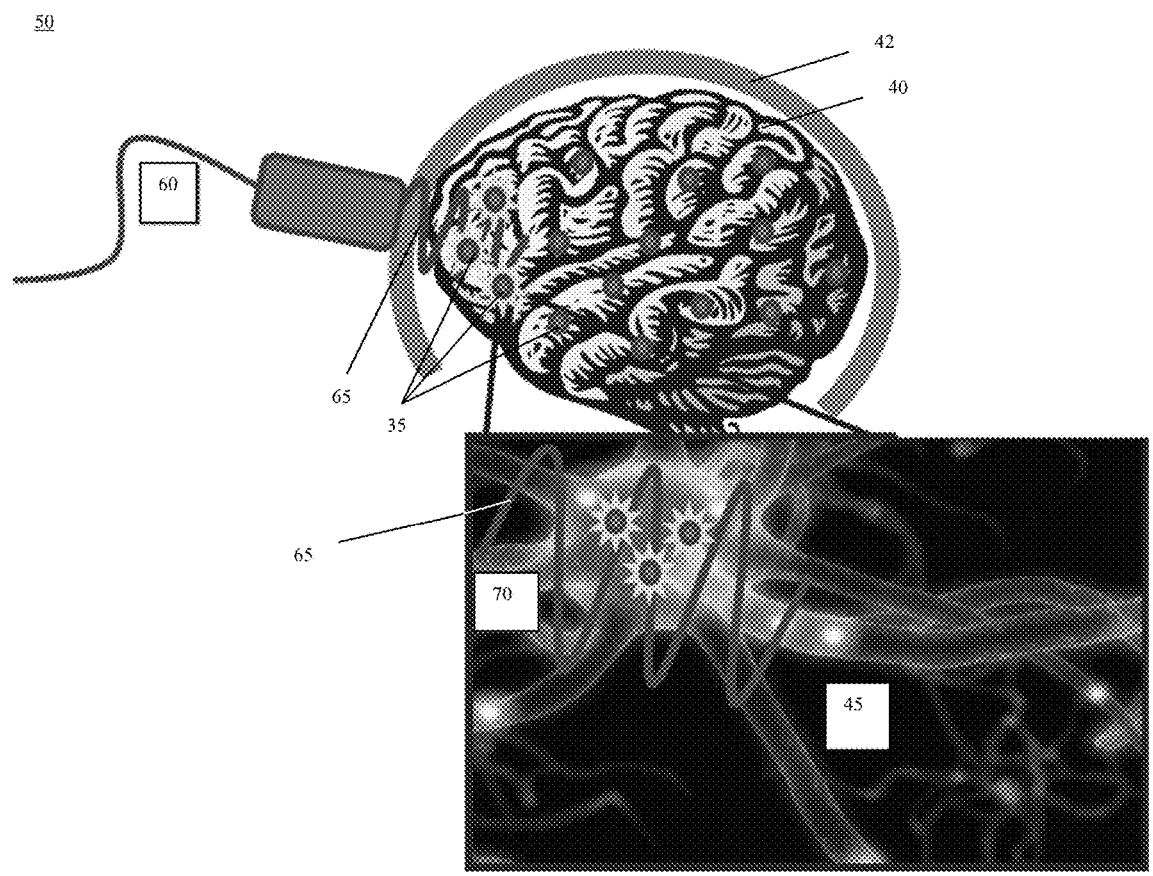
FIG. 2 shows a schematic view of an ultrasonic optogenetic system according to an embodiment of the subject invention.

FIG. 2 shows a schematic view of an ultrasonic optogenetic system 50 according to an embodiment of the subject invention. Referring to FIG. 2, an ultrasound source 60 can provide ultrasound waves 65 to the target (e.g., a mammal brain 40). Light-emitting particles 35 can be provided to the target and can emit light (e.g., visible light) upon stimulation caused by the ultrasound waves 65. The waves 65 can cause vibrations that induce pressure fluctuations 70, and these can cause the light-emitting particles 35 to emit light. Light-sensitive ion channels 45 within the focus area can receive light as a stimulus and open to allow for ion flow, thereby changing the membrane potential and possibly stimulating an action potential. The ultrasound source 60 can deliver vibrations of a frequency that is, for example, on the order of kHz or MHz. In the case of the target being a human brain, the vibrations can penetrate through the skull 45 up to a depth of, for example, 3 cm (or even more).

The light-emitting particles 35 can be chemiluminescent agents, such as fluoresceinyl Cypridina luminescent analog (FCLA), which reacts with oxygen free radicals in air bubbles to emit light, though embodiments are not limited thereto. Such a chemiluminescent agent can emit light by interacting with reactive oxygen species that result from the ultrasonic waves 65 passing through tissue; the interaction can cause a release of chemical energy that alters the structure of the chemiluminescent agent into a brief excited state, with the subsequent relaxation resulting in emission of one or more photons.

The light-sensitive ion channels 45 can open, for example, at least 30% of the time after receiving a single photon as a stimulus. In one embodiment, the light-sensitive ion channels 45 can open about 30%-70% of the time after receiving a single photon as a stimulus. In an alternative embodiment, the light-sensitive ion channels 45 can open at least 70% of the time after receiving a single photon as a stimulus.

In X-ray optogenetic systems and methods of the subject invention, X-rays can be provided to a target sample and converted to visible light. In many embodiments, X-ray-excitable light-emitting particles are used (e.g., through delivery to the target sample). Such light-emitting particles can be, for example, light-emitting NPs (e.g., visible-light-emitting NPs). Specific nanophosphors can absorb X-ray light, thereby promoting a number of resident electrons to higher energy orbitals. These electrons then quickly revert back to their ground-state, emitting light with energy equal to the band gap between the two orbitals in the process. If these nanophosphors are targeted to the rhodopsins inserted into the brain, then the emitted visible light can be close enough to change the properties of the rhodopsins to perform optogenetics. The use of nanophosphors is not required in traditional optogenetics, but it is a beneficial tool that allows optogenetics to be performed deeper into tissue.

The light-emitting particles (e.g., NPs) can be biocompatible and emit light at wavelengths that properly activate the light-sensitive ion channels/pumps. Many nanophosphors can be readily produced with tunable emission, absorbance, and solubility properties. Table 1 lists nanophosphors with emission maxima in the visible domain. With regards to their excitation spectra, two distinct types of nanoparticles can be seen: up-conversion nanoparticles (UCNPs) and UV/X-ray excitable nanoparticles. UCNPs emit visible photons during exposure to long wavelength infrared radiation, while the UV/X-ray excitable particles emit visible photons during exposure to short wavelength UV/X-ray radiation. Particles in the same conversion can be doped with similar ions, though this is not necessary. For example, UCNPs can contain $Yb^{3+}$, $Ln^{3+}$, or Er, while particles sensitive to the shorter wavelength radiation can contain Cr3+, Eu3+, or $Tb^{3+}$. In Table 1, PEG is polyethylene glycol, PAA is poly(acrylic acid), PGA is polyglycolic acid, PEI is polyethylenimine, and DSPE-PEG-COOH is 1,2-distearoyl-sn-glycero-3-phosphoethanolamine[carboxy(polyethyleneglycol)].

Of the NPs in Table 1, most have the excitation wavelength in the range from 147-980 nm. Five NPs have an excitation wavelength of 980 nm, all of which are UCNPs. X-rays have a wavelength range from 0.01-10 nm and therefore cannot efficiently excite these NPs. However, the particles with the base chemistry of $Gd_2O_2S$ and $LiGa_5O_8$ absorb light in both the UV and X-ray ranges. Additionally, these particles can be doped with $Cr^{3+}$, Eu3+, or $Tb^{3+}$. Other particles can also utilize these dopants and can be useful for X-ray excitation.

Certain NPs can be improved for use in X-ray optogenetics (X-optogenetics), especially in the areas of solubility, conversion efficiency, emission, size, and targeting. For example, Table 1 includes NPs that emit light across the visible light spectrum and into the NIR range, with the shortest wavelength emitted at 450 nm and the longest at 800 nm. The emission wavelength is a result of the chemical formula of the NP and the compound with which it is doped. For example, $NaYF_4$ doped with $Eu^{3+}$ has an emission wavelength of 592 nm while $NaYF_4$ doped with $Tb^{3+}$ has an emission wavelength of 545 nm. The ability to alter a nanophosphor's emission wavelength by changing the chemical formula or the compound with which it is doped can be beneficial in optimizing NPs for X-optogenetics. Hybrid doping schemes may also allow for more tailored emission spectra.

types of coatings can be used for the NPs to facilitate X-optogenetics. These coatings can also have a profound effect (e.g., a positive effect) on the ability of the particles to cross the BBB.

In X-optogenetic systems and methods of the subject invention, the placement of the light sources that will be used to generate membrane current in the target neurons can be an important consideration. The proximity of the light-emitting particles (e.g., NPs) in relation to the rhodopsins should be within very short distances as power density is reduced by >90% after 1 mm for all wavelengths of visible

TABLE 1

Nanophosphors.

| Formula | Emission Maximum (nm) | Excitation Wavelength (nm) | Conversion Efficiency (%) | Size (nm) | Dispersible | Toxicity |
|---|---|---|---|---|---|---|
| $Gd_2O_2S: Eu^{3+} (Tb^{3+})$ | 620 (545) | <310 | 15 | 50-300 | Yes, PGA-PEG | Low |
| $Y_2O_3: Eu^{3+}$ | 610 | <310 | 80 | 10-50 | Yes | — |
| $LiGa_3O_2: Cr^{4+}$ | 716 | <310 | — | 50-150 | Yes, PEI | Low |
| $Gd_2O_2S: Yb(8), Er(I)$ | 500-700 | 980 | 25 | 4 μm | Yes | Low |
| $NaMF_4: Yb^{3+}/Ln^{3+}$ | 510-560 | 980 | — | 60 | Yes, DSPE-PEG-COOH | Low |
| $La(OH)_3: Eu^{3+}$ | 597, 615 | 280 | — | 3.5 | Yes, PEG | Low |
| $NaYF_4: Yb/Er$ | 520, 540, 654 | 980 | — | 33 ± 1 | Yes, citrate | — |
| $NaYF_4: 40\%Eu^{3+}$ | 592 | 394 | — | 28 | Yes, PAA | Low |
| $NaYF_4: 40\%Tb^{3+}$ | 545 | 368 | — | 28 | Yes, PAA | Low |
| $cit-NaLnF_4: Yb, Tm$ | 800 | 980 | — | 25 | Yes, citric acid | Low |
| $Ba_2SiO_4$ | 505 | 350 | 38.6 | 40-50 | — | — |
| $Na_2Sr_2Al_2PO_4F_9: Eu^{3-}$ | 593, 619 | 393 | — | 35.26 | — | Non-toxic materials |
| $BaMgAl_{12}O_{17}: Eu^{2-}$ | 450 | 147 | — | 62, 85, 115, 160, 450 | — | — |
| $Sr_2CeO_4$ | 467-485 | 240-360 | — | 45 | — | — |
| $LiCaPO_4: Eu^{2+}_{0.03}$ | 476 | 375 | Quantaum Efficiency: 53.7, 67.6 | — | Yes, PEG-P | — |
| $PEG-Er—Y_2O_3$ | 660 | 980 | — | 30-60 | Yes, PEG | Low |
| $GdVO_4: Eu^{3-}$ | 620 | 330 | — | 6 | Yes | Low |

The conversion efficiency is the ability for the NPs to convert X-ray energy to visible light energy. This is not listed for many of the NPs in Table 1, but it can be an important consideration for X-optogenetic applications. When choosing an NP for X-optogenetics, the conversion efficiency should be as high as possible to reduce the amount of time and X-ray dose to which the subject is exposed. Of course, X-ray stimulation on humans is feasible and safe.

When considering X-optogenetics for neuronal intervention (e.g., use on an animal brain, such as a human brain), the size distribution and coating of the NPs are important for penetration of the phosphors across the blood brain barrier (BBB) to gain access to the cells in the brain. Sizes of particles targeted outside of the central nervous system do not need to be as small, but should still be optimized for maximum bioavailability. Polysorbate-coated nanoparticles can provide high (possibly maximum) passage through the BBB (e.g., for nanoparticles under 100 nm in diameter). Given the sizes of the NPs listed in Table 1 (between 10 nm and 1 μm) and recent advances in nanotechnology, NPs can be obtained with an appropriate size distribution for a range of X-optogenetic applications.

In addition to size, the ability for the particles to be soluble or colloidal in water is a critical property of the NPs as this should add to their biocompatibility. A number of surface coatings, including polyethylene glycol (PEG) and other forms of hydrophilic polymers, can be used to solubilize or suspend the particles in aqueous solutions. These light. One way of inhibiting or preventing this light loss through tissue is to directly target the light-sensitive ion channels/pumps through functionalization of the light-emitting particles (e.g., nanoparticles such as NPs). Small peptide sequences or antibodies can be conjugated and used to enhance cellular uptake or adhesion to the cellular membrane (Gupta et al., Biomaterials 26(18), 3995-4021, Elsevier (2005); De la Fuente et al., Langmuir 22(7), 3286-3293, ACS Publications (2006); and Zhou et al., Photochem. Photobiol. 2006, 82, 1058; all of which are hereby incorporated by reference in their entireties). Using similar methods, the light-emitting particles (e.g., NPs) can be functionalized to specifically bind to the rhodopsins expressed by the target neurons. For example, monoclonal antibodies showing specificity toward ChR2 antigens can be produced by a number of proprietary companies. These antibodies can then be conjugated to the light-emitting particles (e.g., NPs) by reacting their free amine group with the carboxylic acid coating of the light-emitting particles (e.g., NPs). In this way, the proximity issue between the light-sensitive ion channels and the light sources can be minimized, and the light loss due to tissue absorption mitigated.

Table 2 shows an overview for multiple light-sensitive ion channels/pumps. Included are approximate sizes of the channels/pumps that help validate close proximity of NPs and channels/pumps after targeting. NPs that can be used for targeting the ion channels/pumps are also specified.

TABLE 2

Ion Channels/Pumps.

| Ion Channel/Pump | Channelrhodopsin 2 (ChR2) | Halorhodopsin (NphR) | Archeorhodopsin (Arch) |
|---|---|---|---|
| Channel/Pump Mass | 30 kDa | 30 kDa | 28 kDa |
| Minimum Channel/Pump Radius (assuming spherical) | 2.58-2.72 nm | 2.05 nm | 2.00 nm |
| Intensity | 2-20 mW/mm$^2$ | 5.4 ÷ 0.2 mW/mm$^2$ | <10 mW/mm$^2$ |
| Wavelength | 488 nm | 532 nm | 532 nm |
| Pulse Train | 5 ms, 40 Hz | 15 s illumination | 15 s illumination |
| Depolarizing/Hyperpolarizing | Depolarizing | Hyperpolarizing | Hyperpolarizing |
| Possible Nanophosphors | BaMgAl$_{10}$O$_{17}$:Eu$^{2+}$ LiCaPO$_4$:Eu$_{0.03}$$^{2+}$ | Gd$_2$O$_2$S:Tb$^{3+}$ (combination doping?) | Gd$_2$O$_2$S:Tb$^{3+}$ (combination doping?) |
| Hardware Specifications/Involved Components | SOURCE: Carbon Nanotube (peak ~8 keV, pulsing capability) FOCUSING ELEMENT: polycapillary lens OR Fresnel zone plate | | |

In many embodiments, the genetically-modified target neurons can be specifically targeted through functionalization of the light-emitting particles (e.g., NPs), and this can provide a first level of control for neuron activation. In a further embodiment, a second level of control can come from the ability to focus X-rays through the use of a focusing element. The focusing element can be, for example, a lens (e.g., a poly-capillary lens), a zone plate, or a similar focusing means such as a grating. In addition to enhanced control over the neuronal activation, focused X-rays can result in less bulk X-ray dose to the patient, which is always of high concern when dealing with ionizing radiation.

A poly-capillary lens focuses X-rays in the form of an intense microspot using an array of glass micro-capillaries. The size of the focal spot can be, for example, as low as 5 μm. However, for single neuron targeting, focal spots of a few 100 μm can be more applicable. Conventional poly-capillary lenses have a working energy range of 0.5-30 keV. These can be described as soft X-rays and more easily absorbed by the brain tissues. Also, poly-capillary optics can focus higher energy X-rays up to 60 keV, although transmission through these lenses can be low (e.g., <5%) at energies higher than 5 keV.

Excitation of X-ray excitable nanophosphors is described in Cong et al. (X-Ray Fluorescence Computed Tomography With Polycapillary Focusing, Access, IEEE (2014)), which is hereby incorporated by reference in its entirety. X-ray intensity distribution in biological soft tissues can be approximated with inverse distance weighting. In this approximation, $$I(r)=I_0 W(r,r_0)\|r-r_0\|^2, \tag{1}$$

where $r_0$ is the vertex of the double cones, $I_0$ is the intensity of the X-ray source, and $W(r,r_0)$ is the aperture function of the double cones at the vertex $r_0$. For accurate membrane current modulation of the target neurons, the initial intensity of the X-ray source can be adjusted so that the nanophosphors near $r_0$ will receive enough X-ray energy to emit a sufficient number of light photons to activate the rhodopsins. This real-time adjustment also depends on the location of the target neurons as well as the size and fluorescence conversion efficiency of the nanoparticles.

In an embodiment, a Fresnel zone plate (FZP) can be used for more precise focusing of X-rays. FZPs can be micro-fabricated from a soft metal (e.g., gold or nickel), and can modulate either amplitude or phase-shift of incoming X-rays. These modulations can result in a wave diffraction and constructive interference at a focal point. One consideration is that zone plates are typically used for synchrotron produced X-rays. Similar to the poly-capillary lens, zone plates are most effective for X-rays with lower energy levels (e.g., 5-8 keV).

In certain embodiments, light can be delivered in pulses. Such pulses can be, for example, from 5-100 ms each in duration, though embodiments are not limited thereto. With light emitted from the light-emitting particles (e.g., NPs) as they are excited by X-rays, the pulsation comes from the X-ray source itself. Conventional tubes emit X-rays under 10-500 mA current and require several minutes for warming up before emission. Achieving a pulsing emission rate if 5-100 ms/pulse can be difficult or impossible with such a source. A carbon-nanotube field-emission cathode can produce soft X-rays and can be capable of pulsing at high rates for X-optogenetics.

Systems and methods of the subject invention also include those intended for ultrasound optogenetics (U-optogenetics). Sonoluminescence was first discovered in 1934 when air bubbles in a photo-developing solution were seen to emit short bursts of light when subjected to ultrasonic waves. This sonoluminescence effect is due to a cavitation process in which bubbles fill with gas and vapor. Under ultrasonic waves of a specific pressure, collisions between free electrons and ions in the air bubbles cause them to collapse, and these collisions result in thermal bremsstrahlung radiation from electron deflections, which is released as a short burst of light.

Ultrasonic stimulation provides a non-invasive way to stimulate light emission with greater depth than traditional optogenetics. U-optogenetics also has an advantage over X-optogenetics by not delivering ionizing radiation, but it does not equal the penetration distance and focusing power of X-ray techniques.

In certain embodiments of the subject invention, the sonoluminescence effect can be enhanced by the introduction of a chemiluminescent agent. For example, such a chemiluminescent agent can be fluoresceinyl Cypridina luminescent analog (FCLA), which reacts with oxygen free radicals in air bubbles to emit luminescence. Chemiluminescent agents such as FCLA achieve their effect by interacting with reactive oxygen species that result from ultrasonic waves passing through tissue, and this interaction causes a release of chemical energy that alters the structure of the agent. Structural changes induce molecules of the agent into a brief excited state, and the subsequent relaxation results in an emission of photons. For example, under ultrasonic waves with a pressure of 200 kPa, FCLA molecules dissolved in water emit strong chemiluminescence at a peak wavelength of 532 nm with an intensity of 12,580 photons/(cm$^2$-s). This characteristic presents an ideal emission wavelength for use in U-optogenetics.

The chemiluminescent agent (e.g., FCLA) can be targeted close to rhodopsins using a method similar to that discussed herein for X-ray excitable light-emitting particles (e.g., NPs). When subjected to ultrasonic waves, the collapsing air bubbles interacting with the chemiluminescent agent (e.g., FCLA) emit bursts of light to trigger the activation of select rhodopsins.

FIG. 2 illustrates the use of sonoluminescence to stimulate the ion channels. Under these conditions, sonoluminescence provides an alternative excitation pathway in optogenetics. The advantage of ultrasound over X-ray methods is that no radiation dose would be introduced to the patient. However, there is greater attenuation of ultrasonic waves in tissue and bone as compared to X-rays, so penetration depth would be limited. By using low frequency ultrasound waves, penetration depth can be maximized. For ultrasound waves with a frequency of 1 MHz, the penetration depth in bone is approximately 0.3 cm; at a wave frequency of 100 kHz, the penetration depth would increase to approximately 3 cm. Penetration depths of greater than 3 cm through the skull can even be achieved with ultrasound by use of acoustic complementary metamaterials that can cancel out aberrating layers in bone, which could be relevant to scaffold-based experiments.

The U-optogenetic methods and systems can be most effective when the chemiluminescent agent (e.g., FCLA) is most effective at targeting ion channels and pumps directly. Methods similar to those discussed herein for NP targeting can be used to this end.

X-optogenetics and U-optogentics provide several advantages over existing optogenetic approaches. Both are far less invasive and allow for good penetration depth. X-optogenetics in particular allows for penetration to any point in a sample and also for a high level of focus. U-optogenetics provides no radiation dose but cannot penetrate as deeply or focus as sharply as X-optogenetics.

Through functionalization of light-emitting particles, a desirable targeting capability can be achieved that allows for accumulation of the light-emitting particles near the rhodopsins. When choosing the light-emitting particles for X-optogenetics, those with high energy conversion efficiency are preferred as they work with lower X-ray dose, given the maximum power emission for cell stimulation. Further, the size distribution of light-emitting particles can also affect the dose needed to achieve sufficient visible light emission. A Focusing element (e.g., a poly-capillary lens or zone plate) can be used to focus X-rays onto altered cells. The X-ray flux can directly affect the density of the emitted light. Through the use of a carbon nanotube X-ray source rather than a conventional source, a high level of temporal control can be implemented over X-ray excitation, inducing luminescence pulses from the light-emitting particles (e.g., NPs) at suitable frequencies and duty cycles.

The closer the light-emitting particles (e.g., NPs) are to the rhodopsins, the more photons there will be that are able to activate them. Therefore, the light-emitting particles can be targeted to the rhodopsins as specifically as possible. It is possible that only a small number of the proteins will be directly targeted by the light-emitting particles relative to the number expressed in a given cell.

In many optogenetic applications, light stimuli are delivered in sub-second pulse trains over relatively longer periods. In certain embodiments, a CNT X-ray source can be used and can provide millisecond control over the X-ray delivery. While multiple pulses will increase the total effective radiation dose, a single X-ray dose resulting in a single light stimulus can cause lasting membrane voltage modulation in the target neurons. Thus, radiation dose can be minimized if needed. That is, in certain embodiments, a single pulse of X-ray radiation can be provided for stimulation of the light-emitting particles.

As with X-optogenetics, U-optogenetics via sonoluminescence can stimulate ion channels without the need for implanted light sources. Sonoluminescence can be enhanced by a chemiluminescent agent (e.g., FCLA), which can emit bursts of light from air bubbles collapsing under ultrasonic pulses. Targeting of a chemiluminescent agent to ion channels can provide a means for direct stimulation. Also there is no issue with pulse-train application in U-optogenetics because radiation dose is not an issue for this technique.

Without the use of a light probe, X-optogenetics and U-optogenetics are much less invasive and more applicable for research and other applications than related art optogenetic techniques. The decreased invasiveness makes use of optogenetics on humans and/or for applications to features deeper into tissue more feasible. Additionally, the optogenetic techniques of the subject invention are less time-consuming and more ethical than related art techniques because researchers no longer need to surgically drill into the skull of the subject. Moreover, X-optogenetics and U-optogenetics allow for study of parts of the brain that related art optogenetic techniques do not.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The subject invention includes, but is not limited to, the following exemplified embodiments.

Embodiment 1

A method of performing optogenetics, comprising:
providing light-emitting particles to a sample; and
providing X-rays to the sample such that the X-rays cause the light-emitting particles to emit light, thereby changing the membrane potential of a neuron within the sample.

Embodiment 2

The method according to embodiment 1, wherein the light-emitting particles are nanoparticles.

Embodiment 3

The method according to embodiment 2, wherein the light-emitting particles are nanophosphors.

Embodiment 4

The method according to any of embodiments 1-3, wherein the light-emitting particles are visible-light-emitting particles, such that the light-emitting particles emit light in the visible spectrum upon stimulation by the X-rays.

Embodiment 5

The method according to any of embodiments 1-4, wherein providing X-rays to the sample comprises providing X-rays with a carbon nanotube X-ray source.

Embodiment 6

The method according to embodiment 5, wherein the carbon nanotube X-ray source includes a carbon nanotube cathode emitting electrons that are focused onto an anode through at least one of a gate electrode and focusing electrode.

Embodiment 7

The method according to any of embodiments 1-6, wherein the sample is an animal brain.

Embodiment 8

The method according to embodiment 7, wherein the sample is a mammal brain.

Embodiment 9

The method according to embodiment 8, wherein the sample is a human brain.

Embodiment 10

The method according to any of embodiments 1-9, wherein providing X-rays to the sample comprises focusing the X-rays with a focusing element after they are provided by an X-ray source and before they reach the sample.

Embodiment 11

The method according to embodiment 10, wherein the focusing element is a lens.

Embodiment 12

The method according to embodiment 11, wherein the lens is a poly-capillary lens.

Embodiment 13

The method according to embodiment 10, wherein the focusing element is a zone plate.

Embodiment 14

The method according to embodiment 13, wherein the zone plate is a Fresnel zone plate.

Embodiment 15

The method according to embodiment 10, wherein the focusing element is a grating.

Embodiment 16

The method according to any of embodiments 1-15, further comprising providing an X-ray stop or detector on a side of the sample opposite an X-ray source providing the X-rays, in order to collect unabsorbed X-ray radiation.

Embodiment 17

The method according to any of embodiments 1-16, further comprising providing one or more type of rhodopsins to the sample before providing the X-rays, wherein the rhodopsins induce excitatory potentials in neurons of the sample, and wherein the neuron whose membrane potential is changed upon emission of light from the light-emitting particles is among the neurons in which excitatory potentials are induced by the rhodopsins.

Embodiment 18

The method according to embodiment 17, further comprising transfecting neurons of the sample with DNA encoding for a predetermined type of rhodopsin, prior to providing the rhodopsins, wherein providing one or more type of rhodopsins comprises providing the predetermined type of rhodopsin.

Embodiment 19

The method according to any of embodiments 17-18, further comprising functionalizing the light-emitting particles to specifically bind to at least one type of rhodopsin of the one or more type of rhodopsins provided (as recited in embodiment 17).

Embodiment 20

The method according to any of embodiments 17-19, wherein the one or more type of rhodopsins comprises channelrhodopsin2 (ChR2).

Embodiment 21

The method according to any of embodiments 17-20, wherein the one or more type of rhodopsins comprises halorhodpsin (NphR).

Embodiment 22

The method according to any of embodiments 17-21, wherein the one or more type of rhodopsins comprises archeorhodopsin (Arch).

Embodiment 23

The method according to any of embodiments 1-22, wherein changing the membrane potential of a neuron within the sample comprises the opening of a light-sensitive ion channel of the neuron upon receiving at least one photon of the light emitted by the light-emitting particles.

Embodiment 24

A method of performing optogenetics, comprising:
providing chemiluminescent agents to a sample; and
providing ultrasonic waves to the sample causing a sonoluminescence effect within the sample and also causing the chemiluminescent agents to emit light, thereby changing the membrane potential of a neuron within the sample.

Embodiment 25

The method according to embodiment 24, wherein the chemiluminescent agents are fluoresceinyl Cypridina luminescent analog (FCLA) molecules.

Embodiment 26

The method according to any of embodiments 24-25, wherein the chemiluminescent agents emit light in the visible spectrum upon stimulation by the ultrasonic waves.

Embodiment 27

The method according to any of embodiments 24-26, wherein providing ultrasonic waves to the sample comprises providing ultrasonic waves at a frequency on the order of kHz.

Embodiment 28

The method according to any of embodiments 24-26, wherein providing ultrasonic waves to the sample comprises providing ultrasonic waves at a frequency on the order of MHz.

Embodiment 29

The method according to any of embodiments 24-28, wherein the sample is an animal brain.

Embodiment 30

The method according to embodiment 29, wherein the sample is a mammal brain.

Embodiment 31

The method according to embodiment 30, wherein the sample is a human brain.

Embodiment 32

The method according to embodiment 31, wherein the ultrasonic waves penetrate the skull of the human patient having the brain to a depth of at least 0.3 cm.

Embodiment 33

The method according to embodiment 31, wherein the ultrasonic waves penetrate the skull of the human patient having the brain to a depth of about 3 cm.

Embodiment 34

The method according to embodiment 31, wherein the ultrasonic waves penetrate the skull of the human patient having the brain to a depth of at least 3 cm.

Embodiment 35

The method according to embodiment 31, wherein the ultrasonic waves penetrate the skull of the human patient having the brain to a depth of from 0.3 cm to 3 cm.

Embodiment 36

The method according to any of embodiments 24-35, further comprising providing one or more type of rhodopsins to the sample before providing the ultrasonic waves, wherein the rhodopsins induce excitatory potentials in neurons of the sample, and
wherein the neuron whose membrane potential is changed upon emission of light from the light-emitting particles is among the neurons in which excitatory potentials are induced by the rhodopsins.

Embodiment 37

The method according to embodiment 36, further comprising transfecting neurons of the sample with DNA encoding for a predetermined type of rhodopsin, prior to providing the rhodopsins,
wherein providing one or more type of rhodopsins comprises providing the predetermined type of rhodopsin.

Embodiment 38

The method according to any of embodiments 36-37, further comprising functionalizing the chemiluminescent agents to specifically bind to at least one type of rhodopsin of the one or more type of rhodopsins provided (as recited in embodiment 36).

Embodiment 39

The method according to any of embodiments 36-38, wherein the one or more type of rhodopsins comprises channelrhodopsin2 (ChR2).

Embodiment 40

The method according to any of embodiments 36-39, wherein the one or more type of rhodopsins comprises halorhodpsin (NphR).

Embodiment 41

The method according to any of embodiments 36-40, wherein the one or more type of rhodopsins comprises archeorhodopsin (Arch).

Embodiment 42

The method according to any of embodiments 24-41, wherein changing the membrane potential of a neuron within the sample comprises the opening of a light-sensitive ion channel of the neuron upon receiving at least one photon of the light emitted by the light-emitting particles.

Embodiment 43

The method according to any of embodiments 1-42, wherein the light-emitting particles or chemiluminescent agents (as applicable) are coated with a surface coating that helps it pass the blood brain barrier of a human.

Embodiment 44

The method according to embodiment 43, wherein the surface coating is a hydrophilic polymer (e.g., polyethylene glycol).

Embodiment 45

The method according to any of embodiments 1-44, wherein the light-emitting particles or chemiluminescent agents (as applicable) have a largest width (measured in any direction) of at least 150 nm.

Embodiment 46

The method according to any of embodiments 1-44, wherein the light-emitting particles or chemiluminescent agents (as applicable) have a largest width (measured in any direction) of about 150 nm.

Embodiment 47

A kit, comprising:
an X-ray source configured to provide X-ray stimulation;
rhodopsins configured to induce excitatory potentials in neurons of a human brain; and
visible-light-emitting nanophosphors configured to emit visible light upon stimulation from the X-ray source.

Embodiment 48

The kit according to embodiment 48, wherein the nanophosphors are functionalized to specifically bind to the rhodopsins.

Embodiment 49

The kit according to any of embodiments 47-48, further comprising a hydrophilic polymer (e.g., PEG) for using as a surface coating for the nanophosphors.

Embodiment 50

The kit according to any of embodiments 47-49, wherein the nanophosphors have a largest width (measured in any direction) of at least 150 nm.

Embodiment 51

The kit according to any of embodiments 47-49, wherein the nanophosphors have a largest width (measured in any direction) of about 150 nm.

Embodiment 52

The kit according to any of embodiments 47-51, further comprising a focusing element for focusing X-rays provided by the X-ray source.

Embodiment 53

The kit according to embodiment 52, wherein the focusing element is a lens.

Embodiment 54

The kit according to embodiment 53, wherein the lens is a poly-capillary lens.

Embodiment 55

The kit according to embodiment 52, wherein the focusing element is a zone plate.

Embodiment 56

The kit according to embodiment 55, wherein the zone plate is a Fresnel zone plate.

Embodiment 57

The kit according to embodiment 52, wherein the focusing element is a grating.

Embodiment 58

The method according to any of embodiments 47-57, wherein the X-ray source is a carbon nanotube X-ray source.

Embodiment 59

The kit according to embodiment 58, wherein the carbon nanotube X-ray source includes a carbon nanotube cathode for emitting electrons that are focused onto an anode through at least one of a gate electrode and focusing electrode.

Embodiment 60

The kit according to any of embodiments 47-59, further comprising an X-ray stop or detector for collecting unabsorbed X-ray radiation.

Embodiment 61

A kit, comprising:
an ultrasound source configured to provide ultrasonic waves at a frequency on the order of kHz or MHz;
rhodopsins configured to induce excitatory potentials in neurons of a human brain; and
visible-light-emitting chemiluminescent agents configured to emit visible light upon stimulation from the ultrasonic waves.

Embodiment 62

The kit according to embodiment 61, wherein the chemiluminescent agents are functionalized to specifically bind to the rhodopsins.

Embodiment 63

The kit according to any of embodiments 61-62, further comprising a hydrophilic polymer (e.g., PEG) for using as a surface coating for the chemiluminescent agents.

Embodiment 64

The kit according to any of embodiments 61-63, wherein the chemiluminescent agents have a largest width (measured in any direction) of at least 150 nm.

Embodiment 65

The kit according to any of embodiments 61-63, wherein the chemiluminescent agents have a largest width (measured in any direction) of about 150 nm.

Embodiment 66

The kit according to any of embodiments 61-65, wherein the chemiluminescent agents are FCLA molecules.

Embodiment 67

The kit according to any of embodiments 61-66, wherein the ultrasound source is configured to provide ultrasonic waves at a frequency on the order of kHz.

Embodiment 68

The kit according to any of embodiments 61-66, wherein the ultrasound source is configured to provide ultrasonic waves at a frequency on the order of MHz.

Embodiment 69

The method according to any of embodiments 1-46, wherein the X-rays or ultrasonic waves (as applicable) are provided in pulses.

Embodiment 70

The method according to embodiment 69, wherein each pulse has a duration of 5-100 milliseconds (ms).

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

With the involved ionizing radiation for X-optogenetics, it is important to quantify the delivered radiation dose during a procedure. Everyone is generally subject to a baseline effective radiation dose of about 3 mSv a year, but increased levels of radiation exposure occur as a result of X-ray radiography, CT, and PET/SPECT imaging exposure. The effective dose from such a scan can range anywhere from 0.001 mSv-25 mSv. These values depend on the region of exposure, type of radiation, and type of scan. For X-ray related scans, a highest effective dose administered is around 10 mSv. This number was used as the highest effective dose permissible in the following analysis.

Table 2 summarizes the requirements for various rhodopsins. While related art techniques take only a macroscopic view of optogenetics, X-optogenetics can use a micro/nanoscopic scale as well. NPs that are excitable with X-rays can be used, and such NPs should be biocompatible and have a high conversion efficiency. Depending on the NPs used, the X-ray dose can be adjusted. In any case, the NPs should emit visible light that can be used for optogenetics. A CNT, poly-capillary lens, FZP or a similar component can be used to deliver X-rays.

Assuming a maximum effective radiation dose of 10 mSv, a theoretical calculation of power emitted from the nanophosphors chosen from Table 2 was performed. For X-ray radiation, a Sievert (Sv) is defined as 1 Joule (J) of energy per kilogram (kg) of tissue. By definition, 1 J is equal to $6.24 \times 10^{12}$ MeV. Furthermore, the conversion efficiency of $Gd_2O_2S$ particles is about 60,000 visible photons per MeV of absorbed X-ray energy. Using these relationships, the following conversion can be performed $$0.010 Sv \left(\frac{1 \frac{J}{kg\, tissue}}{1\, Sv}\right)\left(\frac{6.24E12\, MeV}{1\, J}\right)\left(\frac{60000\, photons}{1\, MeV}\right) = \qquad (2)$$

$$3.744E6 \frac{photons}{\mu g\, tissue}$$

This conversion is the approximation of photons absorbed per microgram of brain tissue. Then, the number of photons per NP can be approximated. According to the manufacturer, there are about $3.25 \times 10^{13}$ nanophosphors per gram or $3.25 \times 10^7$ per microgram. Using these assumptions, another conversion can be performed.

$$3.744E6 \frac{photons}{\mu g\, tissue}\left(\frac{\mu g\, tissue}{3.25E7\, nanophosphors}\right) = \frac{0.1152\, photons}{nanophosphor} \qquad (3)$$

Less than one photon per NP is not enough to activate a single rhodopsin. However, two of the initial assumptions can be altered to greatly enhance the number of photons per nanophosphor. The first is the phosphor diameter. The NP mass used in the equation was for 50 nm diameter NPs. Simply by increasing the NP diameter by a factor of 3 (to 150 nm), the NP mass can be increased by 27 times ($3^3$), assuming the material density is constant. Increasing the mass results in a proportional decrease of the number of NPs per microgram, yet the conversion efficiency and input energy remain constant. Therefore, output emission is boosted to 3 photons per NP. Further improvement can be achieved by increasing the conversion efficiency of the NPs. The current conversion factor (60,000 photons/MeV) is only 15% as there is enough energy to generate ~400,000 visible photons (496 nm) in one MeV. Therefore, every 5% increase in efficiency is equal to an increase of 20,000 photons. With both of these adjustments, phosphors with a diameter of 150 nm and a quantum efficiency of 50% will emit more than 10 photons per nanophosphor under the acceptable X-ray dose.

In addition, the number of light photons needed to open the light-activated ion channel/pumps was analyzed. To approximate this number, an understanding of the gating mechanism in the proteins is necessary. The light-sensitive moiety of all rhodopsins is a covalently bound derivative of Vitamin A, retinal, that isomerizes under light excitation. The sensitivity of rhodopsins can be defined in part by the quantum efficiency of retinal. This is described as the likelihood of the chromophore to isomerize after absorption of a single photon of light. This efficiency can fall between 30% and 70% in rhodopsins. With this in mind, a single rhodopsin needs between 1.5 and 3 photons of absorbed light to isomerize the retinal molecule and trigger activation of the protein. As calculated herein, by increasing the radius of the particles alone, sufficient numbers of photons can be generated to activate the rhodopsins.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Fenno, L., Yizhar, O., Deisseroth, K., "The development and application of optogenetics," Annu. Rev. Neurosci. 34, 389-412, Annual Reviews (2011).

He, Y., Xing, D., Tan, S., Tang, Y., Ueda, K., "In vivo sonoluminescence imaging with the assistance of FCLA," Phys. Med. Biol. 47(9), 1535, IOP Publishing (2002).

"Optogenetics: Controlling the brain with light.", Tech Tv, MIT News, <http://video.mit.edu/watch/optogenetics-controlling-the-brain-with-light-7659/>.

Adams, A., "Optogenetics earns Deisseroth Keio Prize in Medicine," Stanford Med., 2014, <https://med.stanford.edu/news/all-news/2014/09/optogenetics-earns-deisseroth-keio-prize-inmedieine.html>.

Knopfel, T., Boyden, E. S., Optogenetics: Tools for Controlling and Monitoring Neuronal Activity, Elsevier (2012).

Grossman, N., Poher, V., Grubb, M., Kennedy, G., Nikolic, K., McGovern, B., Berlinguer Palmini, R., Gong, Z., Drakakis, E., et al., "Multi-site optical excitation using ChR2 and micro-LED array," J. Neural Eng 7(1) (2010).

Farah, N., Reutsky, I., Shoham, S., "Patterned optical activation of retinal ganglion cells," Conf Proc IEEE Eng Med Biol Soc (2007).

Lutz, C., Otis, T., DeSars, V., Charpak, S., DiGregorio, D., Emiliani, V., "Holographic photolysis of caged neurotransmitters," Nat Methods 5(9) (2008).

Clements, I. P., Gnadea, A. G., Rusha, A. D., Pattena, C. D., Twomeya, M. C., Kravitzb, A. V., "Miniaturized LED sources for in vivo optogenetic experimentation," Proc. SPIE Vol 8586, 85860X-1 (2013).

Entcheva, E., Williams, J. C., "Channelrhodopsin2 Current During the Action Potential:[ldquo] Optical AP Clamp [rdquo] and Approximation," Sci. Rep. 4, Nature Publishing Group (2014).

Fessenden, J., "EUREKA grant to fund development of new 'optogenetic' technique for mapping neural networks at UMMS," AAAS (2013).

Jagdeo, J. R., Adams, L. E., Brody, N. I., Siegel, D. M., "Transcranial red and near infrared light transmission in a cadaveric model," PLoS One 7(10), e47460, Public Library of Science (2012).

Stolik, S., Delgado, J. A., Perez, A., Anasagasti, L., "Measurement of the penetration depths of red and near infrared light in human 'ex vivo' tissues," J. Photochem. Photobiol. B Biol. 57(2), 90-93, Elsevier (2000).

Sowell, E. R., Thompson, P. M., Leonard, C. M., Welcome, S. E., Kan, E., Toga, A. W., "Longitudinal mapping of cortical thickness and brain growth in normal children," J. Neurosci. 24(38), 8223-8231, Soc Neuroscience (2004).

Shuba, Y. M., "Use of scintillator-based nanoparticles for in vivo control of light-sensitive bioactive molecules," Google Patents (2014).

Sun, C.; Pratx, G.; Carpenter, C. M.; Liu, H.; Cheng, Z.; Gambhir, S. S.; Xing, L. Synthesis and Radioluminescence of PEGylated Eu3+-doped Nanophosphors as Bioimaging Probes. Adv. Mater. 2011, 23, H195-H199.

Stark, G., "X-ray," Encycl. Br. Inc, 2014, <http://www.britannica.com/EBchecked/topic/650351/X-ray>.

"Innovation in Dispersible Nanomaterials.", NanoTech Ocean, 2009, <http://www.oceannanotech.com/product.php?cid=92&pid=286>.

Chen, H., Moore, T., Qi, B., Colvin, D. C., Jelen, E. K., Hitchcock, D. A., He, J., Mefford, O. T., Gore, J. C., et al., "Monitoring pH-triggered drug release from radioluminescent nanocapsules with X-ray excited optical luminescence," ACS Nano 7(2), 1178-1187, ACS Publications (2013).

Moore, T. L., Wang, F., Chen, H., Grimes, S. W., Anker, J. N., Alexis, F., "Polymer-Coated Radioluminescent Nanoparticles for Quantitative Imaging of Drug Delivery," Adv. Funct. Mater. 24(37), 5815-5823, Wiley Online Library (2014).

Gorokhova, E. I., Demidenko, V. A., Mikhrin, S. B., Rodnyi, P. A., Van Eijk, C. W. E., "Luminescence and scintillation properties of Gd2O2S: Tb Ce ceramics," IEEE Trans. Nucl. Sci. 52, (6), 3129-3132, Institute of Electrical and Electronics Engineers (2005).

Jadhav, A. P., Pawar, A. U., Pal, U., Kang, Y. S., "Red emitting Y2O3:Eu3+ nanophosphors with >80% down conversion efficiency†," J. Mater. Chem. C(2), 496-500 (2014).

Dhanaraj, J., Jagannathan, R., Kutty, T. R. N., Lu, C.-H., "Photoluminescence characteristics of Y2O3: Eu3+ nanophosphors prepared using sol-gel thermolysis," J. Phys. Chem. B 105(45), 11098-11105, ACS Publications (2001).

Van Hao, B., Huy, P. T., Khiem, T. N., Ngan, N. T. T., Duong, P. H., "Synthesis of Y2O3: Eu3+ micro- and nanophosphors by sol-gel process," J. Phys. Conf. Ser. 187(1), 12074, IOP Publishing (2009).

Liu, F., Yan, W., Chuang, Y.-J., Zhen, Z., Xie, J., Pan, Z., "Photostimulated near-infrared persistent luminescence as a new optical read-out from Cr3+-doped LiGa5O8," Sci. Rep. 3, Nature Publishing Group (2013).

Chuang, Y.-J., Zhen, Z., Zhang, F., Liu, F., Mishra, J. P., Tang, W., Chen, H., Huang, X., Wang, L., et al., "Photostimulable Near-Infrared Persistent Luminescent Nanoprobes for Ultrasensitive and Longitudinal Deep-Tissue Bio-Imaging," Theranostics 4(11), 1112, Ivyspring International Publisher (2014).

Ajithkumar, G., Yoo, B., Goral, D. E., Hornsby, P. J., Lin, A.-L., Ladiwala, U., Dravid, V. P., Sardar, D. K., "Multimodal bioimaging using a rare earth doped Gd 2 O 2 S: Yb/Er phosphor with upconversion luminescence and magnetic resonance properties," J. Mater. Chem. B 1(11), 1561-1572, Royal Society of Chemistry (2013).

Li, L., Zhang, R., Yin, L., Zheng, K., Qin, W., Selvin, P. R., Lu, Y., "Biomimetic Surface Engineering of Lanthanide-Doped Upconversion Nanoparticles as Versatile Bioprobes," Angew. Chemie 124(25), 6225-6229, Wiley Online Library (2012).

Sun, C., Carpenter, C., Pratx, G., Xing, L., "Facile synthesis of amine-functionalized Eu3+-doped La (OH) 3 nanophosphors for bioimaging," Nanoscale Res. Lett 6, 24 (2011).

Cao, T., Yang, T., Gao, Y., Yang, Y., Hu, H., Li, F., "Water-soluble NaYF4:Yb/Er upconversion nanophosphors: Synthesis, characteristics and application in bioimaging," Inorg. Chem. Commun. 13(3), 392-394 (2010).

Olesiak-Banska, J., Nyk, M., Kaczmarek, D., Matczyszyn, K., Pawlik, K., Samoc, M., "Synthesis andoptical properties of water-soluble fluoride nanophosphors co-doped with Eu3+ and Tb3+," Opt. Mater. (Amst). 33(9), 1419-1423 (2011).

Sun, Y., Peng, J., Feng, W., Li, F., "Upconversion nanophosphors NaluF4: Yb, Tm for lymphatic imaging in vivo by real-time upconversion luminescence imaging under ambient light and high-resolution X-ray CT," Theranostics 3(5), 346, Ivyspring International Publisher (2013).

Chen, J.-Y., Huang, C. K., Hung, W. B., Sun, K. W., Chen, T. M., "Efficiency improvement of Si solar cells using metal-enhanced nanophosphor fluorescence," Sol. Energy Mater. Sol. Cells 120, 168-174 (2014).

Dhoble, S. J., Shinde, K. N., "Ce 3 and Eu 3 activtated Na2Sr2Al2PO4F9 nanophosphor."

Yadav, R. S., Pandey, S. K., Pandey, A. C., "Blue-Shift and Enhanced Photoluminescence in BaMgAl10O17: Eu2+ Nanophosphor under VUV Excitation for PDPs Application," Mater. Sci. Appl. 1(01), 25, Scientific Research Publishing (2010).

Niyaz Parvin Shaik, N. V. Poornachandra Rao, B. Subba Rao, and K. V. R. M., "Photoluminescence Studies on Sr2CeO4 Nanophosphor," Wourld J. Chem., 114-117 (2011).

Minsung, K., Makoto, K., Hideki, K., Masato, K., "A Highly Luminous LiCaPO 4: Eu 2+ Phosphor Synthesized by a Solution Method Employing a Water-Soluble Phosphate Ester," Opt. Photonics J. 2013, Scientific Research Publishing (2013).

Zako, T., Nagata, H., Terada, N., Sakono, M., Soga, K., Maeda, M., "Improvement of dispersion stability and characterization of upconversion nanophosphors covalently modified with PEG as a fluorescence bioimaging probe," J. Mater. Sci. 43(15), 5325-5330, Springer (2008).

Dong, K., Ju, E., Liu, J., Han, X., Ren, J., Qu, X., "Ultrasmall biomolecule-anchored hybrid GdVO 4nanophosphors as a metabolizable multimodal bioimaging contrast agent," Nanoscale 6(20), 12042-12049, Royal Society of Chemistry (2014).

Ahmad, M., Pratx, G., Bazalova, M., Xing, L., "X-ray luminescence and x-ray fluorescence computed tomography: new molecular imaging modalities," IEEE.

Gao, K., Jiang, X., "Influence of particle size on transport of methotrexate across blood brain barrier by polysorbate 80-coated polybutylcyanoacrylate nanoparticles.," Int. J. Pharm. 310(1-2), 213-219 (2006).

Chatterjee, K., Sarkar, S., Jagajjanani Rao, K., Paria, S., "Core/shell nanoparticles in biomedical applications," Adv. Colloid Interface Sci. 209, 8-39, Elsevier (2014).

Yizhar, O., Fenno, L. E., Davidson, T. J., Mogri, M., Deisseroth, K., "Optogenetics in neural systems," Neuron 71(1), 9-34, Cell Press (2011).

Gupta, A. K., Gupta, M., "Synthesis and surface engineering of iron oxide nanoparticles for biomedical applications," Biomaterials 26(18), 3995-4021, Elsevier (2005).

De la Fuente, J. M., Berry, C. C., Riehle, M. O., Curtis, A. S. G., "Nanoparticle targeting at cells," Langmuir 22(7), 3286-3293, ACS Publications (2006).

Zhou, J.; Xing, D.; Chen, Q. Enhancement of Fluoresceinyl Cypridina Luciferin Analog Chemiluminescence by Human Serum Albumin for Singlet Oxygen Detection. *Photochem. Photobiol.* 2006, 82, 1058.

Zhou, Y., Drummond, D. C., Zou, H., Hayes, M. E., Adams, G. P., Kirpotin, D. B., Marks, J. D., "Impact of single-chain Fv antibody fragment affinity on nanoparticle targeting of epidermal growth factor receptorexpressing tumor cells," J. Mol. Biol. 371(4), 934-947, Elsevier (2007).

Dbrowski, K. M., Dul, D. T., Korecki, P., "X-ray imaging inside the focal spot of polycapillary optics using the coded aperture concept," Opt. Express 21(3), 2920-2927, Optical Society of America (2013).

Romanov, A. Y., "Optic parameters of a middle-focus Kumakhov lens for hard X-rays," Tech. Phys. Lett. 31(3), 200-201, Springer (2005).

Cong, W., Xi, Y., Wang, G., "X-Ray Fluorescence Computed Tomography With Polycapillary Focusing," Access, IEEE (2014).

Di Fabrizio, E., Romanato, F., Gentili, M., Cabrini, S., Kaulich, B., Susini, J., Barrett, R., "High-efficiency multilevel zone plates for keV X-rays," Nature 401(6756), 895-898, Nature Publishing Group (1999).

Yue, G. Z., Qiu, Q., Gao, B., Cheng, Y., Zhang, J., Shimoda, H., Chang, S., Lu, J. P., Zhou, O., "Generation of continuous and pulsed diagnostic imaging x-ray radiation using a carbon-nanotube-based field-emission cathode," Appl. Phys. Lett. 81(2), 355 (2002).

"Radiation Dose in X-Ray and CT Exams.", Radiol. Soc. North Am. Inc., 2014, <http://www.radiologyinfo.org/en/safety/?pg=sfty_xray>.

Nagel, G., Szellas, T., Huhn, W., Kateriya, S., Adeishvili, N., Berthold, P., Ollig, D., Hegemann, P., Bamberg, E., "Channelrhodopsin-2, a directly light-gated cation-selective membrane channel," Proc. Natl. Acad. Sci. 100(24), 13940-13945, National Acad Sciences (2003).

"Agrisera Antibodies Product Information.", <http://www.agrisera.com/cgibin/ibutik/SkapaFaktura.pl?SkrivPDF=J&funk=visa_artikel&artnr=AS12 1851 &Friendly_Grupp=bacterialinsect-and-fungal-&Friendly=nphr-halorhodopsin-&artgrp=28&Sprak=en>(11 May 2014).

Uegaki, K., Sugiyama, Y., Mukohata, Y., "Archaerhodopsin-2, from <i>Halobacterium</i> sp. aus-2 further reveals essential amino acid residues for light-driven proton pumps," Arch. Biochem. Biophys. 286(1), 107-110, Elsevier (1991).

Erickson, H. P., "Size and shape of protein molecules at the nanometer level determined by sedimentation, gel filtration, and electron microscopy," Biol. Proced. Online 11(1), 32-51, Springer (2009).

Arenkiel, B. R., Peca, J., Davison, I. G., Feliciano, C., Deisseroth, K., Augustine, G. J., Ehlers, M. D., Feng, G., "In vivo light-induced activation of neural circuitry in transgenic mice expressing channelrhodopsin-2," Neuron 54(2), 205-218, Elsevier (2007).

Raimondo, J. V., Kay, L., Ellender, T. J., Akerman, C. J., "Optogenetic silencing strategies differ in their effects on inhibitory synaptic transmission," Nat. Neurosci. 15(8), 1102-1104, Nature Publishing Group (2012).

"Energy and Work Unit Conversion.", Advameg, Inc., 2014, <http://www.unitconversion.info/energy.html>(11 Oct. 2014).

Barber, T. E. D., Brockway, J. A., Higgins, L. S., "The density of tissues in and about the head," Acta Neurol. Scand. 46(1), 85-92, Wiley Online Library (1970).

Hegemann, P., Moglich, A., "Channelrhodopsin engineering and exploration of new optogenetic tools," Nat. Methods 8(1), 39-42, Nature Publishing Group (2011).

Frenzel, J., Schultes, H., "Luminescence in water carrying supersonic waves," Z. Phys. C 27, 421-424 (1934).

Hilgenfeldt, S., Grossmann, S., Lohse, D., "A simple explanation of light emission in sonoluminescence," Nature 398(6726), 402-405, Nature Publishing Group (1999).

Christensen, D. A., "Ultrasonic bioinstrumentation, 1988," JW Sons, New York.

Shen, C., Xu, J., Fang, N. X., Jing, Y., "Anisotropic Complementary Acoustic Metamaterial for Canceling out Aberrating Layers," Phys. Rev. X 4(4), 41033, American Physical Society (2014).

Jia, Z., Valiunas, V., Lu, Z., Bien, H., Liu, H., Wang, H.-Z., Rosati, B., Brink, P. R., Cohen, I. S., et al., "Stimulating Cardiac Muscle by Light Cardiac Optogenetics by Cell Delivery," Circ. Arrhythmia Electrophysiol. 4(5), 753-760, Am Heart Assoc (2011).

Berndt, A., Lee, S. Y., Ramakrishnan, C., Deisseroth, K., "Structure-Guided Transformation of Channelrhodopsin into a Light-Activated Chloride Channel," Science (80-.). 344(6182), 420-424, American Association for the Advancement of Science (2014).

Christensen, D. A. *Ultrasonic bioinstrumentation*; JW Sons: New York, N.Y., USA, 1988.

Zhang, J., Yang, G., Cheng, Y., Gao, B., Qiu, Q., Lee, Y. Z., Lu, J. P., Zhou, O., "Stationary scanning x-ray source based on carbon nanotube field emitters," Appl. Phys. Lett. 86(18), 184104, AIP Publishing (2005).

Kaulitzki, S., "aktive nervenzelle," Fotolia.

Microsoft., "Illustration of the human brain," Microsoft.

Mattis, J.; Tye, K. M.; Ferenczi, E. A.; Ramakrishnan, C.; O'Shea, D. J.; Prakash, R.; Gunaydin, L. A.; Hyun, M.; Fenno, L. E.; Gradinaru, V. Principles for applying optogenetic tools derived from direct comparative analysis of microbial opsins. *Nat. Methods* 2012, 9, 159-172.

Shen, C.; Xu, J.; Fang, N. X.; Jing, Y. Anisotropic Complementary Acoustic Metamaterial for Canceling out Aberrating Layers. *Phys. Rev. X* 2014, 4, 41033.

Jia, Z.; Valiunas, V.; Lu, Z.; Bien, H.; Liu, H.; Wang, H.-Z.; Rosati, B.; Brink, P. R.; Cohen, I. S.; Entcheva, E. Stimulating Cardiac Muscle by Light Cardiac Optogenetics by Cell Delivery. Circ. *Arrhythmia Electrophysiol.* 2011, 4, 753-760.

Berndt, A.; Lee, S. Y.; Ramakrishnan, C.; Deisseroth, K. Structure-Guided Transformation of Channelrhodopsin into a Light-Activated Chloride Channel. *Science* (80-.). 2014, 344, 420-424.

Zhang, J.; Yang, G.; Cheng, Y.; Gao, B.; Qiu, Q.; Lee, Y. Z.; Lu, J. P.; Zhou, O. Stationary scanning x-ray source based on carbon nanotube field emitters. *Appl. Phys. Lett.* 2005, 86, 184104.

What is claimed is:

1. A method of performing optogenetics, comprising:
functionalizing light-emitting particles to specifically bind to at least one type of rhodopsin;
providing the light-emitting particles to a sample including the at least one type of rhodopsin; and
providing X-rays to the sample with a carbon nanotube X-ray source including a focusing element, such that the X-rays cause the light-emitting particles to emit light, thereby changing the membrane potential of a neuron within the sample through the action of the rhodopsin;
wherein the light-emitting particles have a diameter of about 150 nm and wherein the carbon nanotube X-ray source is configured to achieve a pulsing emission rate of 5 to 100 milliseconds per pulse;
wherein changing the membrane potential of the neuron within the sample comprises the opening of a light-sensitive ion channel of the neuron upon receiving at least one photon of the light emitted by the light-emitting particles;
wherein the light-sensitive ion channel opens at least 30% of the time after receiving one photon of the light emitted by the light-emitting particles.

2. The method according to claim 1, wherein the light-emitting particles are visible- light-emitting nanophosphors, such that the nanophosphors emit light in the visible spectrum upon stimulation by the X-rays.

3. The method according to claim 1, wherein the carbon nanotube X-ray source includes a carbon nanotube cathode emitting electrons that are focused onto an anode through at least one of a gate electrode and focusing electrode.

4. The method according to claim 1, wherein the sample is an animal brain.

5. The method according to claim 1, wherein providing X-rays to the sample comprises focusing the X-rays with the focusing element after they are provided by an X-ray source and before they reach the sample, wherein the focusing element is a poly-capillary lens, a Fresnel zone plate or a grating.

6. The method according to claim 1, further comprising providing one or more type of rhodopsins to the sample before providing the X-rays, wherein the rhodopsins induce excitatory or inhibitory potentials in neurons of the sample,
wherein the neuron whose membrane potential is changed upon emission of light from the light-emitting particles is among the neurons in which excitatory potentials are induced by the rhodopsins,
wherein the method further comprises transfecting neurons of the sample with DNA encoding for a predetermined type of rhodopsin, prior to providing the rhodopsins,
wherein providing one or more type of rhodopsins comprises providing the predetermined type of rhodopsin, and
wherein the one or more type of rhodopsins comprises at least one of channelrhodopsin2 (ChR2), halorhodpsin (NphR), and archeorhodopsin (Arch).

7. The method according to claim 1, wherein the light-emitting particles are coated with a surface coating that helps it pass the blood brain barrier of a human.

* * * * *